US006774276B1

(12) United States Patent
Lund et al.

(10) Patent No.: US 6,774,276 B1
(45) Date of Patent: Aug. 10, 2004

(54) METHOD AND SYSTEM FOR TRANSPORTING A FLOW OF FLUID HYDROCARBONS CONTAINING WATER

(75) Inventors: Are Lund, Trondheim (NO); David Lysne, Trondheim (NO); Roar Larsen, Ranheim (NO); Kai W. Hjarbo, Ranheim (NO)

(73) Assignee: Sinvent AS, Trondheim (NO)

( * ) Notice: Subject to any disclaimer, the term of this patent is extended or adjusted under 35 U.S.C. 154(b) by 0 days.

(21) Appl. No.: 09/807,841

(22) PCT Filed: Sep. 21, 1999

(86) PCT No.: PCT/NO99/00293

§ 371 (c)(1), (2), (4) Date: Jun. 29, 2001

(87) PCT Pub. No.: WO00/25062

PCT Pub. Date: May 4, 2000

(30) Foreign Application Priority Data

Oct. 27, 1998 (NO) ........................................ 1998 5001

(51) Int. Cl.[7] ............................ C10G 33/00; C07C 7/20

(52) U.S. Cl. ......................... 585/899; 585/15; 208/187; 208/188; 137/13

(58) Field of Search ..................... 585/15, 899; 137/13; 422/198, 224, 234; 208/187, 188

(56) References Cited

U.S. PATENT DOCUMENTS

| | | | | | |
|---|---|---|---|---|---|
| 3,514,274 | A | * | 5/1970 | Cahn et al. | 48/190 |
| 5,055,178 | A | | 10/1991 | Sugier et al. | |
| 5,536,893 | A | * | 7/1996 | Gudmundsson | 585/15 |
| 5,816,280 | A | * | 10/1998 | Rojey et al. | 137/3 |
| 6,028,234 | A | * | 2/2000 | Heinemann et al. | 585/15 |
| 6,082,118 | A | * | 7/2000 | Endrizzi et al. | 62/46.1 |
| 6,180,843 | B1 | * | 1/2001 | Heinemann et al. | 585/15 |
| 6,350,928 | B1 | * | 2/2002 | Waycuilis et al. | 585/15 |

FOREIGN PATENT DOCUMENTS

| | | |
|---|---|---|
| EP | 0082630 | 6/1983 |

* cited by examiner

*Primary Examiner*—Walter D. Griffin
*Assistant Examiner*—Tam M. Nguyen
(74) *Attorney, Agent, or Firm*—Wenderoth, Lind & Ponack, L.L.P.

(57) ABSTRACT

A method of transporting a flow of fluid hydrocarbons containing water through a treatment and transportation system including a pipeline, wherein the flow of fluid hydrocarbons is introduced into a reactor where it is mixed with particles of gas hydrates which are also introduced into the reactor. The effluent flow of hydrocarbons from the reactor is cooled in a heat exchanger to ensure that all water present therein is in the form of gas hydrates. The flow is then treated in a separator to be separated into a first flow and a second flow. The first flow has a content of gas hydrate and is recycled to the reactor to provide the particles of gas hydrates mentioned above. The second flow is conveyed to a pipeline to be transported to its destination.

14 Claims, 2 Drawing Sheets

METHOD AND SYSTEM FOR TRANSPORTING A FLOW OF FLUID HYDROCARBONS CONTAINING WATER

BACKGROUND OF THE INVENTION

1. Field of the Invention

The present invention relates to a method and a system for transporting a flow of fluid (i.e. liquid or gaseous) hydrocarbons containing water. In the method the flow is transported through a treatment and transportation system including a pipeline.

2. Description of Related Art

The search for new oil or gas resources has now reached a stage where it is moving away from relatively easily accessible continental waters, and towards deeper waters. This trend is currently most visible in the Gulf of Mexico, but also offshore Norway, and any large oil or gas discoveries in the future are primarily expected in deep waters (≧4–500 m). This development gives rise to several technological challenges. However, solutions based on sub-sea installations and long distance transport to already existing production and processing facilities have already been in use for some time in the North Sea, especially in connection with economically marginal fields in the vicinity of older platforms. This technology will become steadily more prevalent in new field developments for deep water, but also in the increasing number of smaller projects in already developed areas.

Traditionally, in the North Sea, use of sub-sea templates and pipeline transport of the well-stream in multiphase pipelines has been restricted to a few tens of kilometers. However, better simulation and design tools, better equipment for partial separation, as well as pumping and boosting, has now led to solutions of this kind being used with transfer distances of up to 110 km in the Gulf of Mexico.

The single most challenging problem for these future trends in oil and gas exploration, is the presence of natural gas hydrates in transport pipelines and equipment. Natural gas hydrate is an ice-like compound consisting of light hydrocarbon molecules encapsulated in an otherwise unstable water crystal structure. These hydrates form at high pressures and low temperatures wherever a suitable gas and free water are present. These crystals can deposit on pipeline walls and in equipment, and in the worst case lead to complete plugging of the system. Costly and time-consuming procedures may be needed to restore flow again. In addition to the mere economic consequences, there are also numerous hazards connected to hydrate formation and removal, and there are known instances of pipeline ruptures and loss of human lives due to gas hydrates in pipelines. Although hydrate is generally thought of as a problem mostly for gas production, there is now ample evidence that it is also a significant problem for condensate and oil production systems.

There are several available methods for dealing with hydrate problems. So far, the usual philosophy has been to take steps to avoid any hydrate formation at all. This can be achieved by keeping pressures low (often not possible from flow considerations), keeping temperatures high (usually by insulating—which does not protect against shutdowns or long distances), removing the water completely (costly equipment and difficult), or by adding chemicals that suppress hydrate formation thermodynamically. Insulation is very often used, but is not sufficient alone. Chemical addition, specifically methanol (MeOH) or ethylene glycol (EG), is therefore the most widespread hydrate control mechanism in the industry today. These antifreezes expand the pressure-temperature-area of safe operation, but are needed in large quantities—50% of the total liquid fraction is not unusual in water-rich production. The use of MeOH in the North Sea may approach 3 kg per 1000 $Sm^3$ of gas extracted. The need for such large amounts places severe demands on logistics of transportation, storage and injection in offshore facilities with a deficiency of space. The transport and injection processes for MeOH in particular, are also plagued with numerous leakages and spills.

Inhibitor chemicals of different types are not only used in the pipeline transport and processing areas, but also extensively in drilling operations and wells.

Partly due to the huge amounts and large costs involved in using traditional inhibitors like MeOH, there has over the last decade been extensive efforts devoted to finding chemicals which may be effective at controlling hydrates at much lower concentrations.

Many oil companies and research institutes have contributed to this effort, and at present, the results are divided into three main categories: kinetic inhibitors, dispersants, and modificators. Kinetic inhibitors have an affinity for the crystal surface, and thereby can be used to prevent hydrate crystal growth. Dispersants act as emulsifiers, dispersing water as small droplets in the hydrocarbon liquid phase. This limits the possibilities for hydrate particles to grow large or to accumulate. The modificators are to a certain extent a combination of the two other methods, attaching to the crystal surface, but also functioning as a dispersant in the liquid hydrocarbon phase. These methods have been somewhat successful, although there are practical drawbacks to most of them. The most significant problem, however, seems to be that all the best chemical additives thus far produced have significant negative environmental effects, and that no solution to this problem seems imminent—at least in the open literature.

There is growing understanding in the oil and gas industry that hydrate particles in a flow situation are not necessarily a problem per se. If the particles do not deposit on walls or equipment, and do not have a large impact on flow characteristics (i.e. their concentration is not too large), they simply flow with the rest of the fluids, without creating a problem situation. The challenge will therefore be to achieve this situation in a controlled manner, and making sure that hydrate formation does not take place randomly throughout the flow system.

Another aspect which will definitely be affected by the present invention, is corrosion in sub-sea pipelines. Huge sums of money and large resources in material and time are involved in protecting pipelines from corrosion, e.g. through conservative design (pipeline wall thickness, steel quality) and through the use of corrosion inhibitors. Not necessarily used in the same amounts per pipeline as the hydrate inhibitors, the total amounts of chemicals (sometimes with environmentally highly adverse effects) are huge, as they are used in such a great number of pipelines. Much of this corrosion is connected with free water, and successful results of the present invention may reduce this problem significantly.

SUMMARY OF THE INVENTION

The present invention provides a method for transporting a flow of fluid hydrocarbons containing water through a treatment and transportation system including a pipeline. According to the invention the flow of fluid hydrocarbons is introduced into a reactor where it is mixed with particles of gas hydrates which are also introduced into the reactor, the effluent flow of hydrocarbons from the reactor is cooled in a heat exchanger to ensure that all water present therein is in the form of gas hydrates. The flow is then treated in a separator to be separated into a first flow and a second flow, said first flow having a content of gas hydrates is recycled to the reactor to provide the particles of gas hydrates mentioned above, and the second flow is conveyed to a pipeline to be transported to its destination.

The flow of fluid hydrocarbons will normally come from a drilling hole well and will be relatively warm and will be under pressure. It is generally preferred to cool the flow of fluid hydrocarbons in a first heat exchanger before introducing The flow into the above-mentioned reactor.

It is sometimes desirable to add certain chemicals to the flow upstream to the reactor.

Before the flow enters the reactor it may advantageously be subjected to a mixing operation in order to disperse the water present as droplets in the fluid hydrocarbon phase.

The second flow from the separator may be mixed with wet gas in a mixing vessel before the flow is conveyed to the pipeline for further transport.

The method is particularly applicable in those cases where transportation takes place at a relatively low temperature, both on land in a cool climate and at the sea bottom.

When the surroundings are rather cool, one or more of the heat exchangers used may be an uninsulated pipe. When the surrounding temperature is sufficiently low, this will provide satisfactory cooling without any further cooling medium.

The invention also provides a system for treatment and transportation of a flow of fluid hydrocarbons containing water. The system includes the following elements listed in the flow direction and connected with each other so that the hydrocarbons may pass through the entire system (the numerals in parenthesis refer to the enclosed drawings which serve as illustration only):

- connection to a hydrocarbon source (1),
- a first heat exchanger (4),
- a reactor (6),
- a second heat exchanger (7),
- a separator (8), and
- a pipeline (13);
- and in addition a line (9) which leads from the separator (8) to the reactor (6) and is provided with a pump (10) adapted to recycle material from the separator (8) back to the reactor (6). The pump may be any kind of pump, but it may advantageously be of a type which crushes the hydrate particles into more and smaller particles with a larger total crystal surface.

The inside of the system, in particular the inside of the reactor may be coated with a water repellent material. Tubing may also advantageously be provided with such a coating material.

The system preferably includes a mixer or a choke (5) upstream to the reactor (6).

In many cases it is advantageous to add different chemicals to the flow of hydrocarbons, in particular during start-up and when changes are made in the operation. The system accordingly contains for such purpose means for adding chemicals to the flow.

BRIEF DESCRIPTION OF THE DRAWINGS

In the following the present method and system will be described in more detail, again with reference to the drawings.

DETAILED DESCRIPTION OF THE INVENTION

Figure 1:
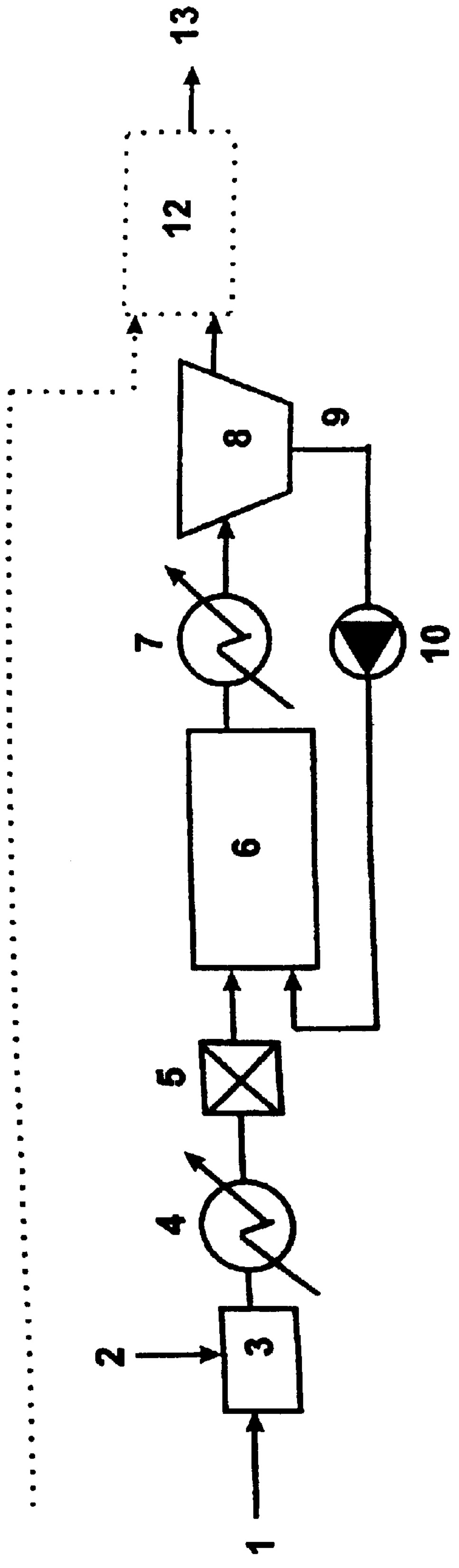
FIG. 1 is a schematic illustration of a first embodiment of a method for transporting a flow of fluid hydrocarbons containing water in accordance with the present invention.

In a first embodiment (FIG. 1) warm oil/condensate/hydrate-forming components and water under pressure (1) are mixed with any desired chemicals (2) in a mixing means (3). If much water is initially present, some of the water is preferably separated off before mixing the components and water with chemicals. The chemicals in question may be nucleating agents for hydrate, emulsion-breakers/-formers, wax inhibitors or any type of chemical used for transportation/storage of the fluid. The chemicals used should be acceptable for the environment and should generally be used during start-up only. In any case the consumption of chemicals will be much lower during continuous operation than previous transportation/storage systems, and chemicals may even be left out completely.

The fluid from the mixer (3) may be cooled to a temperature just above the hydrate equilibrium curve of the fluid (the melting curve of hydrate) in a heat exchanger (4). At the bottom of the ocean the heat exchanger may be an uninsulated tube, or it may be any type of cooler.

The fluid from the heat exchanger (4) is conveyed to a mixer (5) which may be any type of mixer. The mixer distributes the water in the fluid hydrocarbons as droplets. It should be noted that the mixer is not strictly necessary. The question whether or not a mixing operation is necessary depends on the characteristics of the fluid, i.e. the ability of the fluid to distribute the water as droplets in the fluid without any other influence than the turbulence which occurs when the fluid flows through a pipe.

The fluid from the mixer (5) is conveyed into a reactor (6), where it is mixed with cold (temperature below the melting temperature of the gas hydrate) fluid from a separator (8) (see below). The cold fluid from the separator (8) contains small particles of dry hydrate.

The water which is present in the fluid from the mixer (5) will moisten dry hydrate from the separator (8) in the reactor (6). In the reactor (6) the water which moistens the dry hydrate, will immediately be converted to hydrate. New hydrate which is formed will accordingly increase the size of the hydrate particles from the separator (8) and also form new small hydrate particles when larger hydrate particles break up. New hydrate seed may also be formed elsewhere in the reactor (6).

Sub-cooling (the actual temperature being lower than the hydrate equilibrium temperature) of the fluid is required to form hydrates. The necessary extent of sub-cooling for formation of hydrate in the reactor (6) is accomplished by adding sufficient cold fluid from the separator (8). Cooling may also come from the reactor walls of the reactor (6) or from separate cooling ribs in the reactor. Undesired fouling or formation of deposits in the reactor (6) may be avoided by coating all surfaces with a water-repellent coating.

From the reactor (6) the fluid is cooled down in a second heat exchanger (7). At the bottom of the ocean the cooler may be an uninsulated pipe. The heat exchanger (7) may also be any type of cooler which even may be integrated as a part of the reactor (6).

In the separator (8) some of the total amount of hydrate particles and excess fluid are separated from the rest and conveyed out to a pipeline (13) or first through a mixing means (12) to be mixed with wet gas (11) before entering the pipeline (13).

Residual amounts of the total amount of hydrate particles and residual fluid from the separator (8) are recycled through a line (9) by means of a pump (10) back to the reactor (6). The separator (8) may be any type of separator. Similarly, the pump (10) may be any type of pump, but it is important that it can handle the hydrate particles. It may advantageously be of a type which crushes the hydrate particles into more and smaller particles with a larger total crystal surface. A further cooler may be included in the line (9) either before or behind the pump (10).

Wet gas (11) under pressure may be mixed with the flow of fluid from the separator (8) in a mixing means (12). Free water in the wet gas is absorbed by the dry hydrate from the separator (8) in the mixing means (12). In the mixing means (12) the water which moistens the dry hydrate will readily be converted to hydrate. The new hydrate formed will then increase the size of the hydrate particles from the separator (8) and may also form new small hydrate particles when larger hydrate particles are broken apart. New hydrate seed may also be formed elsewhere in the mixing means (12). At the outlet of the mixing means (12) connected to the pipeline (13) all free water has been converted to hydrate.

At the beginning of the pipeline, either sub-sea at a wellhead template, or onboard a minimum processing platform, water separation is expected to be efficient enough so that after cooling and condensation, no more than 5–10 vol % water is present in the fluid stream.

After this separation stage, the fluids are cooled rapidly towards hydrate stability temperatures in exposed (uninsulated) pipes of the necessary length. The phases are also mixed, to provide a large interfacial surface area. Minute amounts of chemicals may be needed at this stage, e.g. in connection with a start-up situation. A mixer will disperse the water as droplets. Upon next entering the hydrate reactor part of the system, hydrate particles and a cold fluid stream are mixed in from a downstream separator. Water wetting of the hydrate will take place, and hydrate growth will therefore mainly be from existing particles and outwards. The hydrate formation process is thus aided by the addition of cold fluid (inside the stable hydrate pressure-temperature region), and—most important—the already present hydrate particles. Further cooling takes place through the reactor.

Figure 2:
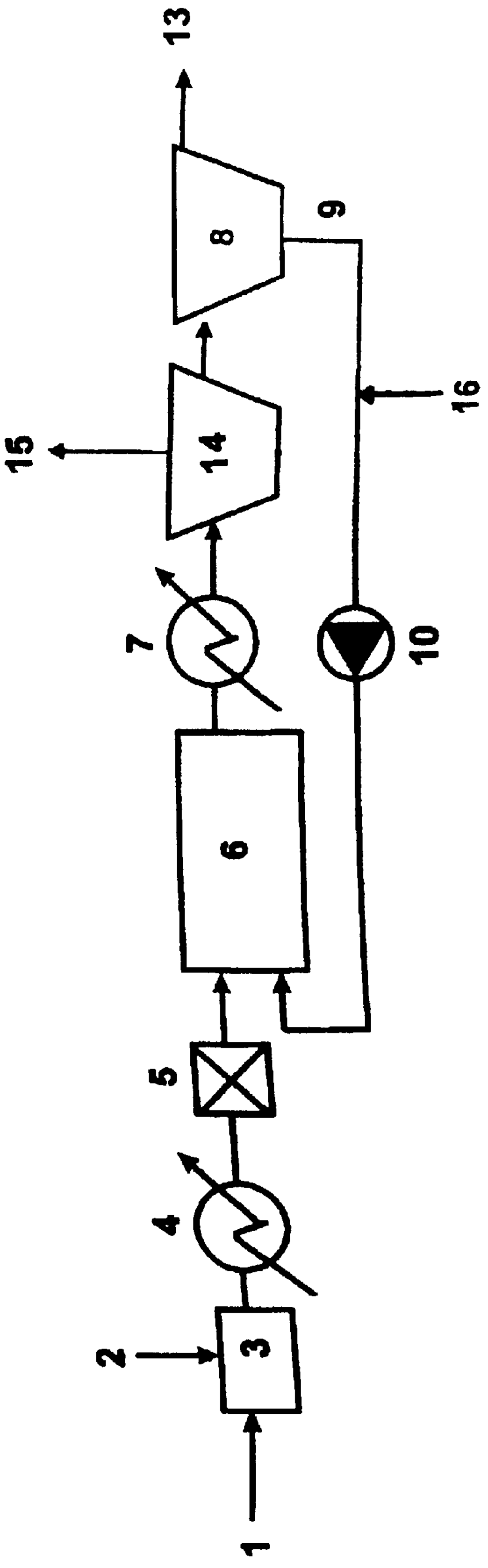
FIG. 2 is a schematic illustration of a second embodiment of the present invention.

According to a second embodiment (see FIG. 2) the fluid hydrocarbon is preferably a wet hydrocarbon gas. The method of this embodiment is particularly applicable at the sea bottom.

To a great extent the discussion of the first embodiment above will also apply to this second embodiment. In the following, particularly those features which are more or less different will be discussed.

Warm hydrocarbon gas (1) under pressure is mixed with any desired chemicals (2) in a mixing means (3). Chemicals may also be added to the system in the reactor (6).

The flow from the mixer (3) may be cooled to a temperature just above the hydrate equilibrium curve of the flow (the melting curve of hydrate) in a heat exchanger (4) and/or through a choke (5) which may be a part of the reactor (6). At the bottom of the ocean the heat exchanger may be an uninsulated tube, or it may be any type of cooler.

The flow from the choke (5) is conveyed into the reactor (6), where it is mixed with cold (temperature below the melting temperature of the gas hydrate) fluid from a second separator (8) (see below). The cold fluid from the separator (8) contains small particles of dry hydrates.

Free water and water condensing from hydrocarbon gas in the flow from the choke (5) will moisten dry hydrate from the separator (8) in the reactor (6). In the reactor (6) the water which moistens the dry hydrate will immediately be converted to hydrate. New hydrate which is formed will accordingly increase the size of the hydrate particles from the separator (8) and also form new small hydrate particles when larger hydrate particles break up. New hydrate seed may also be formed elsewhere in the reactor (6).

In a first separator (14) hydrocarbon gas is separated from the flow and conveyed out to a pipeline (15). The separator (14) may be any type of separator.

The rest of the flow is conveyed to the second separator (8) where some of the total amount of hydrate particles and excess fluid are separated from the rest and conveyed out to a pipeline (13).

Residual amounts of the total amount of hydrate particles and residual fluid from the separator (8) are recycled through a line (9) by means of a pump (10) back to the reactor (6). The separator (8) may be any type of separator. Similarly, the pump (10) may be any type of pump, but it is important that it can handle the hydrate particles.

Additional cooled condensate under pressure may be added (16) to the recycled flow in order to dilute the hydrate particle concentration and as a cooling media. The addition may be made at any point between heat exchanger (7) and reactor (6).

Hot hydrocarbon gas, either sub-sea at a wellhead template, or from a minimum processing platform, is expected to be saturated with water vapour at the beginning of the pipeline.

After the wellhead template or platform, the flow is cooled rapidly towards hydrate stability temperature in exposed (uninsulated) pipes of the necessary length or through a choke. Minute amounts of chemicals may be needed at this stage, e.g. in connection with a start-up situation. Upon entering the hydrate reactor part of the system, hydrate particles and cold fluid stream, are mixed in from a downstream separator. Water vapour from the hydrocarbon gas phase will condense and water wetting of the hydrate particles will take place. From this stage hydrate growth will therefore mainly take place from existing particles. The hydrate formation process is thus aided by the addition of cold fluid (inside the stable hydrate pressure-temperature region), and-most important—the already present hydrate particles. Further cooling takes place through the reactor. Hydrocarbon fluid condensed from the cooled hydrocarbon gas will add to the fluid in the reactor.

A further, general discussion of the present invention is given in the following.

Free water in the pipeline proper will tend to act as a "bonding agent" between hydrate and pipe walls. The inner surface of the hydrate reactor can be treated to become non-wetting with respect to water.

All of the water in the stream will be converted to dry hydrate particles by the time it reaches the end of the hydrate reactor. Before the stream reaches the downstream separator it is cooled close to ambient temperature in exposed (uninsulated) pipes of necessary length. In the separator some of the cold hydrocarbon fluids and dry hydrate particles are taken out, and re-injected at the reactor inlet, as described above.

If injection of wet gas (from the initial separation stage) is desirable, it may take place after the separation/ recirculation point (8), into the stream with fully converted hydrates. These fluids may then flow through a similar hydrate reactor to achieve full conversion before the main pipeline. However, no separation and recirculation is viewed as necessary for this stage.

The main pipeline starts immediately after the separator or the wet gas hydrate reactor.

With the water being in hydrate form, and the hydrate particles being dry (no excess water) it has been known experimentally in flow loops with both model systems and with real field fluids and pressures and temperatures, that the resulting hydrate powder is easily transportable with the liquid flow. These tests also indicated that the particles will not aggregate or deposit on pipe walls or equipment—not even in the case of longtime shut-downs. This particular phenomenon has been studied by the inventors for several years. It is also a great advantage of the present invention that the absence of free water will reduce the risk of corrosion in pipelines and other installations.

The hydrate powder will not melt back to free the water and natural gas until temperatures rise or pressures become too low—which in reality will be at the end of the transport pipe, where the process will not be problematic. The powder can be mechanically separated from the bulk liquid phase by a sieve (unlike dispersant-induced emulsions which are often difficult to break). Another method would be to melt the hydrates in a separator where the residence time is long enough for the emerging water to separate out from the hydrocarbon liquids. Depending on the fluid system, the particle density may even deviate enough from the bulk liquid so that the particles may easily be separated off.

The present invention is expected to create considerable positive environmental effects. The development of a safe and efficient way to transport free water in the form of hydrate particles will dramatically reduce the need for a host of different chemical additives which are used today, both hydrate and corrosion inhibitors. This will impact all aspects of the hydrocarbon production process, from working conditions on production and processing facilities, to the effect on the environment through leaks, accidental discharges or injection system malfunctioning.

A secondary, but no less important, environmental effect will be the improved safety aspects in pipeline operation: with the hydrate plugging and corrosion risks minimized, the danger of pipeline ruptures and large-scale blowouts will also be lowered. It should also be noted that a pipeline in thermal equilibrium with its surroundings will be safer with respect to melting of hydrates in the surrounding sediments which may induce instabilities (settling and landslides). This aspect is in addition to the fact that a cold fluid stream without temperature-induced changes in the fluid composition and properties makes the whole pipeline a more well-defined system to operate. This will not cause additional problems in itself, as pipeline transport over any significant distance will eventually reach ambient temperature also in traditional transport solutions.

The very limited use of chemicals according to the present invention also has the effect that the flow of fluid hydrocarbons is more suitable for its final use than known from the prior art. Thus, e.g. antifreeze such as methanol may have to be removed before the hydrocarbons are used in different processes, such as for polymerization purposes. Such removal is generally very costly.

What is claimed is:

1. A method for transporting a flow of fluid hydrocarbons containing water through a treatment and transportation system including a pipeline, the method comprising:

introducing the flow of fluid hydrocarbons into a reactor, wherein the flow of fluid hydrocarbons contains water;

introducing a cold fluid flow of hydrocarbons, containing particles of gas hydrates acting as a hydrophilic agent, into the reactor where it is mixed with the flow of fluid hydrocarbons containing water;

cooling an effluent flow of hydrocarbons from the reactor in a heat exchanger to ensure that free water present therein attains the form of gas hydrates;

treating the cooled effluent flow in a separator to separate the flow into a first flow and a second flow, wherein the first flow has a content of gas hydrate;

recycling the first flow to the reactor to provide the particles of gas hydrate; and conveying the second flow to a pipeline to be transported to a destination.

2. The method as claimed in claim 1, wherein the flow of fluid hydrocarbons containing water is cooled in a first heat exchanger before being introduced into the reactor.

3. The method as claimed in claim 1, further comprising adding chemicals upstream of the reactor.

4. The method as claimed in claim 1, wherein the flow of fluid hydrocarbons containing water is subjected to a mixing operation before being introduced into the reactor to disperse the water present as droplets in the fluid hydrocarbon phase.

5. The method as claimed in claim 1, wherein the said second flow from the separator is mixed with wet gas before it is conveyed to the pipeline.

6. The method as claimed in claim 1, wherein the method is performed at the bottom of the sea.

7. The method as claimed in claim 1, wherein an uninsulated pipe is used as the heat exchanger when the surrounding temperature is lower than a hydrate equilibrium temperature for the fluid mixture.

8. The method as claimed In claim 1, wherein the fluid hydrocarbons are hydrocarbon gas containing water.

9. The method as claimed in claim 1, further comprising conveying the hydrocarbon flow through a choke which is arranged upstream of the reactor or is a part of the reactor.

10. The method as claimed in claim 1, wherein the flow from the reactor is conveyed through a first separator to be separated into a hydrocarbon gas flow and a flow which is subsequently subjected to separation into the first flow and the second flow.

11. The method as claimed in claim 10, further comprising adding cooled condensate under pressure to the first flow which is recycled to the reactor.

12. The method as claimed in claim 2, further comprising adding chemicals upstream of the reactor.

13. The method as claimed in claim 2, wherein the flow of fluid hydrocarbons containing water is subjected to a mixing operation before being introduced into the reactor to, disperse the water present as droplets in the fluid hydrocarbon phase.

14. The method as claimed in claim 3, wherein the flow of fluid hydrocarbons containing water is subjected to a mixing operation before being introduced into the reactor to disperse the water present as droplets in the fluid hydrocarbon phase.

* * * * *